US010857032B2

(12) United States Patent
Motwani

(10) Patent No.: US 10,857,032 B2
(45) Date of Patent: Dec. 8, 2020

(54) SYSTEMS AND METHODS FOR CORNEAL LASER ABLATION

(71) Applicant: Manoj Motwani, San Diego, CA (US)

(72) Inventor: Manoj Motwani, San Diego, CA (US)

(*) Notice: Subject to any disclaimer, the term of this patent is extended or adjusted under 35 U.S.C. 154(b) by 301 days.

(21) Appl. No.: 15/949,885

(22) Filed: Apr. 10, 2018

(65) Prior Publication Data
US 2018/0289545 A1 Oct. 11, 2018

Related U.S. Application Data

(60) Provisional application No. 62/502,538, filed on May 5, 2017, provisional application No. 62/484,706, filed on Apr. 12, 2017, provisional application No. 62/484,331, filed on Apr. 11, 2017.

(51) Int. Cl.
*A61F 9/008* (2006.01)
*A61B 3/10* (2006.01)
*A61B 3/14* (2006.01)
*A61B 3/107* (2006.01)

(52) U.S. Cl.
CPC .......... *A61F 9/00806* (2013.01); *A61B 3/102* (2013.01); *A61B 3/1005* (2013.01); *A61B 3/107* (2013.01); *A61B 3/14* (2013.01); *A61F 2009/00872* (2013.01); *A61F 2009/00882* (2013.01)

(58) Field of Classification Search
CPC ........ A61F 9/00806; A61F 2009/00872; A61F 2009/00882; A61B 3/1005; A61B 3/102; A61B 3/107; A61B 3/14
See application file for complete search history.

(56) References Cited

U.S. PATENT DOCUMENTS

| 4,923,467 A | 5/1990 | Thompson |
| 2002/0026180 A1 | 2/2002 | Nakamura |
| 2005/0107775 A1* | 5/2005 | Huang .................... A61F 9/008 606/5 |
| 2007/0161972 A1 | 7/2007 | Felberg et al. |

(Continued)

FOREIGN PATENT DOCUMENTS

| EP | 1034756 A2 | 9/2000 |
| EP | 2683287 B1 | 2/2017 |

(Continued)

OTHER PUBLICATIONS

"Moving from Rx to Measured." EyeWorld; May 2017 (May 7, 2017): 1-8. US-WVL-17-E-1093 http://supplements.eyeworld.org/h/i/344076942-ew-may-2017-sunday-supported-by-alcon-a-novartis-division.

(Continued)

*Primary Examiner* — Lindsey G Wehrheim
(74) *Attorney, Agent, or Firm* — Veros Legal Solutions, LLP

(57) ABSTRACT

Systems and methods for corneal laser ablation for primary vision correction include topographic guided ablation. A laser ablation pattern for removal of astigmatism is derived at least in part from corneal topographic data rather than manifest astigmatism. Laser ablation patterns for treatment of high order aberrations of the cornea may also be based on corneal topographic data. Spherical corrections may be based on manifest refraction, eye models, or wavefront aberrometry.

23 Claims, 11 Drawing Sheets
(5 of 11 Drawing Sheet(s) Filed in Color)

(56) References Cited

U.S. PATENT DOCUMENTS

| | | | |
|---|---|---|---|
| 2007/0260157 A1* | 11/2007 | Norrby | A61B 3/0025 600/558 |
| 2007/0282313 A1 | 12/2007 | Huang et al. | |
| 2008/0249514 A1 | 10/2008 | Hohla et al. | |
| 2008/0287929 A1 | 11/2008 | Holliday et al. | |
| 2009/0268213 A1* | 10/2009 | Blalock | A61B 3/1005 356/521 |
| 2009/0299347 A1 | 12/2009 | Vogler et al. | |
| 2011/0202045 A1 | 8/2011 | Youssefi | |
| 2011/0238045 A1 | 9/2011 | Dick et al. | |
| 2011/0276043 A1 | 11/2011 | Youssefi et al. | |
| 2013/0204237 A1 | 8/2013 | Fabrikant | |
| 2014/0028979 A1 | 1/2014 | Juan et al. | |
| 2014/0268057 A1 | 9/2014 | Hacker et al. | |
| 2015/0018674 A1 | 1/2015 | Scott et al. | |
| 2015/0131054 A1 | 5/2015 | Wuellner et al. | |
| 2016/0095752 A1 | 4/2016 | Srinivasan et al. | |
| 2016/0150952 A1 | 6/2016 | Raymond et al. | |

FOREIGN PATENT DOCUMENTS

| | | |
|---|---|---|
| EP | 3135261 A1 | 3/2017 |
| WO | 2015003739 A1 | 1/2015 |
| WO | 2016126333 A1 | 8/2016 |
| WO | 2018191267 A1 | 10/2018 |

OTHER PUBLICATIONS

"LENSTAR LS 900 Improving Outcomes." 9. Edition / Aug. 2016. Haag-Streit Diagnostics. Koeniz, Switzerland.

"Schwind Cam Perfect Planning—wide range of applications." (2018) Schwind Eye-Tech-Solutions. Kleinostheim, Germany.

"Schwind Diagnostic Devices—Experience a new Level of Convenience." (2017) Schwind Eye-Tech-Solutions. Kleinostheim, Germany.

Bhatt, et al. Comparison of Predictions Made by the Intraocular Lens Master and Ultrasound Biometry. Arch Ophthalmol. 2008;126(7):929-933. doi:10.1001/archopht.126.7.929.

Chen, et al. Postoperative Changes in Corneal Epithelial and Stromal Thickness Profiles After Photorefractive Keratectomy in Treatment of Myopia. J Refract Surg. Jul. 2015;31(7):446-53. doi: 10.3928/1081597X-20150623-02.

Cummings, A. & McGuire, C. "Ray Tracing for Laser Corneal Refractive Surgery" Ot Refractive Surgery Clinical, Feb. 7, 2010.

Handbook of Optical Systems: vol. 4 Survey of Optical Instruments. Edited by Herbert Gross. (2008) Wiley-VCH Verlag GmbH & Co. KGaA, Weinheim. ISBN: 978-3-527-40380-6.

Hou, J., et al. "Corneal Epithelial Remodeling and Its Effect on Corneal Asphericity after Transepithelial Photorefractive Keratectomy for Myopia." Journal of ophthalmology (Jul. 28, 2016).

Huang, D. & Tang, M. & Shekhar, R. (2003). Mathematical model of corneal surface smoothing after laser refractive surgery. American journal of ophthalmology. 135. 267-78. 10.1016/S0002-9394(02)01942-6.

Kanellopoulos, et al. "Correlation between Epithelial Thickness in Normal Corneas, Untreated Ectatic Corneas, and Ectatic Corneas Previously Treated with CXL; Is Overall Epithelial Thickness a Very Early Ectasia Prognostic Factor?" Clinical Ophthalmology (Auckland, N.Z.) 6 (May 22, 2012): 789-800. PMC. Web. Apr. 27, 2018.

Kent, C. "Topography-guided Ablation: Pros and Cons". (Jul. 5, 2012) R. of Opthamology. https://www.reviewofophthalmology.com/article/topography-guided-ablation-pros-and-cons.

Lin, H. & Chen, C. & Lee, Y. (2013). Comparisons of wavefront refraction, autorefraction, and subjective manifest refraction. Tzu Chi Medical Journal. 25. 43-46. 10.1016/j.tcmj.2013.01.006.

Meek, K. & Knupp, C. (2015). Corneal Structure and Transparency. Progress in Retinal and Eye Research. vol. 49. pp. 1-16. doi.org/10.1016/j.preteyeres.2015.07.001.

Motwani, M. (May 16, 2017). The use of WaveLight Contoura to create a uniform cornea: the LYRA Protocol. Part 1: the effect of higher-order corneal aberrations on refractive astigmatism. Clinical Ophthalmology. vol. 11. 897-905. 10.2147/OPTH.S133839.

Motwani, M. (May 16, 2017). The use of WaveLight Contoura to create a uniform cornea: the LYRA Protocol. Part 2: the consequences of treating astigmatism on an incorrect axis via excimer laser. Clinical Ophthalmology. vol. 11. 907-913. 10.2147/OPTH.S133840.

Motwani, M. (May 16, 2017). The use of WaveLight Contoura to create a uniform cornea: the LYRA Protocol. Part 3: the results of 50 treated eyes. Clinical Ophthalmology. vol. 11. 897-905. 10.2147/OPTH.S133839.

Motwani, M. (Mar. 23, 2017) "A protocol for topographic-guided corneal repair utilizing the US Food and Drug Administration-approved Wavelight Contoura." Clinical ophthalmology.

Pokupec, R. et al. "Comparison between refractometer and retinoscopy in determining refractive errors in children—false doubt." Collegium antropologicum 37 Suppl 1 (2013): 205-8.

Reinstein, D Z. et al. "Comparison of Corneal Epithelial Thickness Measurement Between Fourier-Domain OCT and Very High-Frequency Digital Ultrasound." Journal of refractive surgery (Thorofare, N.J.☐: 1995) 31.7 (2015): 438-445. PMC. Web. Apr. 27, 2018.

Reinstein, D. Z. et al. "Accuracy of refractive outcomes in myopic and hyperopic laser in situ keratomileusis: Manifest versus aberrometric refraction." Journal of cataract and refractive surgery 38 11 (2012): 1989-95.

Tang, M. & Li, Y. & Huang, D.. (2015). Corneal Epithelial Remodeling after LASIK Measured by Fourier-Domain Optical Coherence Tomography. Journal of Ophthalmology. 2015. 1-5. 10.1155/2015/860313.

Toda, et al. "Visual Outcomes After LASIK Using Topography-Guided vs Wavefront-Guided Customized Ablation Systems." J Refract Surg. Jun. 23, 2016 Nov. 1;32(11):727-732. doi: 10.3928/1081597X-20160718-02. PubMed PMID: 27824375.

Vojniković, B., & Tamajo, E. (2013). Gullstrand's optical schematic system of the eye—modified by Vojniković & Tamajo. Collegium antropologicum, 37 Suppl 1, 41-5.

Wang, Q. et al. (2012) "A Comprehensive Assessment of the Precision and Agreement of Anterior Corneal Power Measurements Obtained Using 8 Different Devices." PloS one.

International Search Report and Written Opinion dated Aug. 2, 2018 in International Patent Application No. PCT/US2018/026900.

\* cited by examiner

SYSTEMS AND METHODS FOR CORNEAL LASER ABLATION

RELATED APPLICATIONS

This application claims priority to provisional applications 62/484,331 filed on Apr. 11, 2017, 62/484,706 filed on Apr. 12, 2017, and 62/502,538 filed on May 5, 2017. Each of these applications is incorporated by reference in its entirety.

BACKGROUND

Three fundamental components of the human eye as shown in FIG. 1A are the cornea 12, the lens 14, and the retina 16. The optical axis 18 of the eye is an imaginary line passing through the peak of the cornea 12 and the foveal region of the retina 16. Ideally, light rays within a few millimeters of and parallel to the optical axis 18 that are incident to a relaxed eye will enter the cornea 12, pass through the lens 14 and will be focused essentially on a single point on the foveal region of the retina 16. The refractive power of the eye is typically measured in diopters, and is the reciprocal of the focal length of the lens system formed by the cornea 12 and lens 14. Ideally, the power of the eye is such that the focal length is close to the axial length 20 of the eye. Typically, human eyes have a power of approximately 60 diopters, with about 40 diopters in the cornea and about 20 diopters in the lens. Most of the 40 diopters of the cornea is provided by the anterior surface of the cornea at the air-corneal interface, and the shape and topography of the anterior corneal surface is in many cases a significant determinant of vision quality.

The cornea itself includes multiple histologically distinct layers. As shown in FIG. 1B, these include the epithelium 32 on the anterior surface, the stroma 34 below that, and the endothelium 36 on the posterior surface. The thickness of the stroma may typically be about 90% of the total thickness of the cornea 12. Common refractive errors of the eye include myopia, hyperopia, and astigmatism. With myopia, the corneal surface curvature may be spherical, but the curvature and hence the power is too large. With hyperopia, the corneal surface curvature may also be spherical, but the curvature and hence the power is too small. With astigmatism, the curvature of the anterior corneal surface may form a non-spherical football type contour, with a different radius of curvature in different directions from the peak. For example, as shown in FIG. 1C, the corneal surface could have a maximum power $K_1$ in a first direction, and a minimum power $K_2$ in a direction orthogonal to that. Although there are different ways to numerically represent it, a characterization of an astigmatic eye may include two values, one related to the two powers $K_1$ and $K_2$, (e.g. the difference between $K_1$ and $K_2$) and an axis angle defining the deviation from horizontal of the flatter meridian ($K_2$ in FIG. 1C).

As an alternative to glasses or contacts, various forms of eye surgery have been developed to address myopia, hyperopia, and astigmatism. Recently, selective laser ablation of the corneal surface has become popular in the form of PRK and LASIK to correct these vision problems. In early versions of this procedure, as shown in FIG. 2A, an examination of a patient with, for example, a phoropter 44 would be performed to generate a "manifest" refraction measurement. With a phoropter, by looking through a sequence of different lenses and determining which corrections look best to the patient in terms of perceived visual quality, sphere and cylinder corrections are found that compensate for the patient's myopia, hyperopia, and/or astigmatism. These corrections are input to a laser system 42, and the laser system 42 develops laser ablation parameters to re-shape the cornea 12 in accordance with the phoropter determined sphere and cylinder corrections. He laser system then applies laser energy to the corneal surface to selectively ablate the corneal surface in accordance with the determined parameters.

More recently, a technique known as wavefront guided laser surgery has been developed. Referring to FIG. 2B, an instrument called a wavefront aberrometer 46 is used to characterize the properties of the patient's eye. These instruments may shine a pattern of spots onto the retina, and the retina reflected wavefront that exits the eye is detected. As the spot pattern travels into the eye and back out again, the pattern is changed, and detecting these changes can characterize the total optical aberrations introduced into the light beams by the optical elements and interfaces of the patient's eye.

These aberrations are typically characterized by the coefficients of polynomials called Zernike polynomials (although other representations such as Fourier series can also be used). Myopia, hyperopia, and astigmatism are characterized by coefficients of second order Zernike polynomials. Optical aberrations of the eye can also include aberrations characterized by coefficients of third and higher order Zernike polynomials, and may be referred to as high order aberrations (HOA). High order aberrations characterized by Zernike polynomials include aberrations known as coma, trefoil, quadrafoil, and spherical aberration.

By using many points of light in the pattern, aberrations of second order and aberrations of higher than second order can be detected by the wavefront aberrometer, which allows for the characterization of the optical properties of the patient's eye in more detail than just sphere and cylinder corrections that are obtained with a phoropter. With both lower order and higher order characterizations of the optical properties of the eye, the laser system 42 generates an ablation pattern that modifies the corneal surface in a way that is designed to compensate for the aberrations detected in the entire optical system of the eye.

SUMMARY

In one implementation, a corneal laser ablation system comprises a corneal topography measuring instrument and a laser system configured to emit pulsed laser light at one or more wavelengths and configured to control the parameters of laser emission such that the laser output is suitable for controlled ablation of an anterior corneal surface. The laser system is configured to control the laser output to ablate at least some high order aberrations from the anterior corneal surface in accordance with topographical measurements of the anterior corneal surface made with the corneal topography measuring instrument. The laser system is configured to control the laser output to ablate the anterior corneal surface in a manner that reduces astigmatism of the anterior corneal surface in accordance with a corneal astigmatism derived at least in part from the topographical measurements of the anterior corneal surface made with the corneal topography measuring instrument.

In another implementation, a method of correcting corneal aberrations in an eye of a subject, the method comprises measuring a topography of a corneal surface of the subject, obtaining a measurement of corneal astigmatism that is derived at least in part from the measured topography of the corneal surface, planning a corneal laser ablation procedure based at least in part on the measurement of corneal astigmatism that is derived at least in part from the measured topography of the corneal surface, and performing corneal laser ablation on the corneal surface of the subject in accordance with the planning.

In another implementation, a corneal laser ablation system comprises a corneal topography measuring instrument and an axial eye length measuring instrument. The system also comprises a laser system configured to emit pulsed laser light at one or more wavelengths and configured to control the parameters of laser emission such that the laser output is suitable for controlled ablation of an anterior corneal surface. The laser system is configured to control the laser output to ablate a portion of the anterior surface of a cornea based at least in part on both one or more topographical measurements of the anterior corneal surface made with the corneal topography measuring instrument and one or more axial eye length measurements made by the axial eye length measuring instrument.

BRIEF DESCRIPTION OF THE DRAWINGS

The patent or application file contains at least one drawing executed in color. Copies of this patent or patent application with color drawing(s) will be provided by the Office upon request and payment of the necessary fee.

DETAILED DESCRIPTION

Figure 1C:
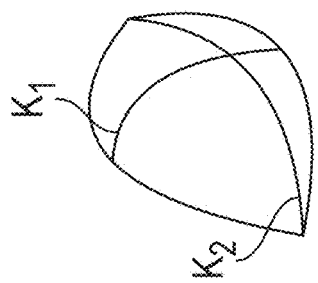
FIG. 1C is a diagram illustrating an astigmatic eye.
Figure 1A:
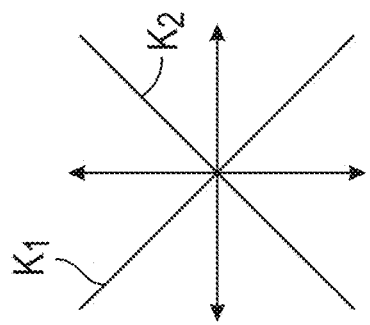
FIG. 1A is a cross section of eye anatomy.
Figure 1A:
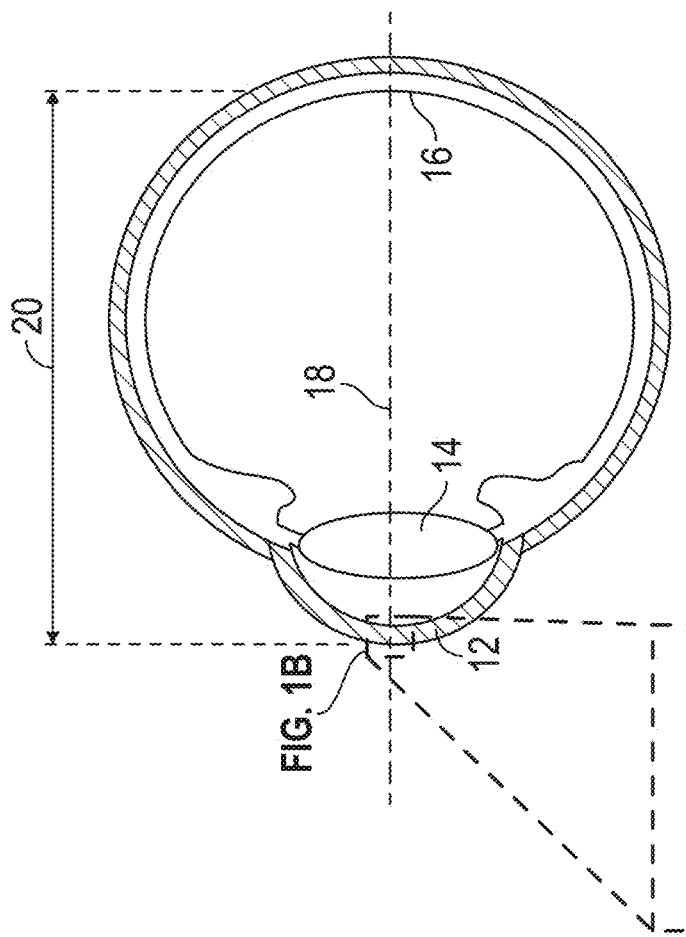

A better understanding of the various features of the disclosure can be gleaned from the following description read in conjunction with the accompanying drawings in which like reference characters refer to like elements, where reasonably applicable. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this disclosure to possess a described meaning, there is no intent to limit the meaning of such term, either expressly or indirectly, beyond its plain or ordinary meaning.

As introduced above, in many refractive correction procedures, selective laser ablation applied to the anterior corneal surface may be used to reduce or correct optical aberrations such as those described above. A newer technique has recently been introduced to the field of laser eye surgery known as topographic guided ablation. Initially used for repair of damaged, diseased, or otherwise abnormal corneas, the use of topographic guided ablation for primary refractive correction on patients with otherwise normal corneas is a relatively new concept.

Figure 2A:
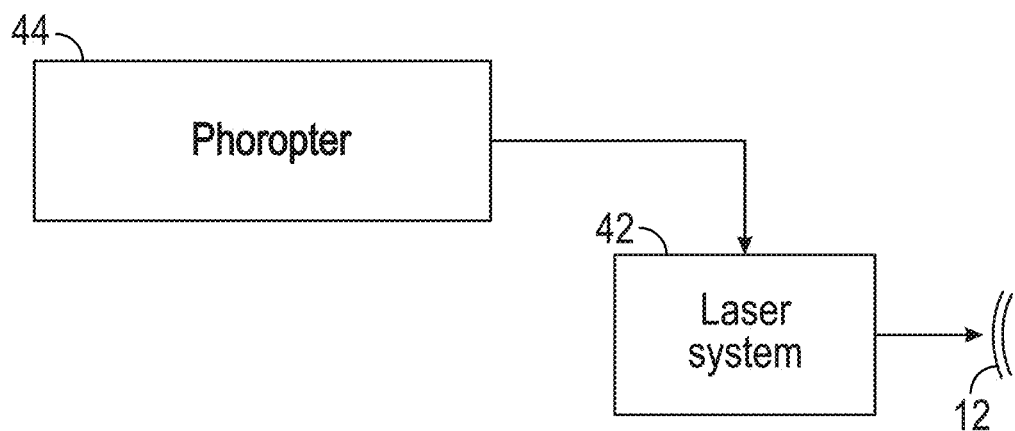
FIG. 2A is a prior art corneal laser ablation system.
Figure 2B:
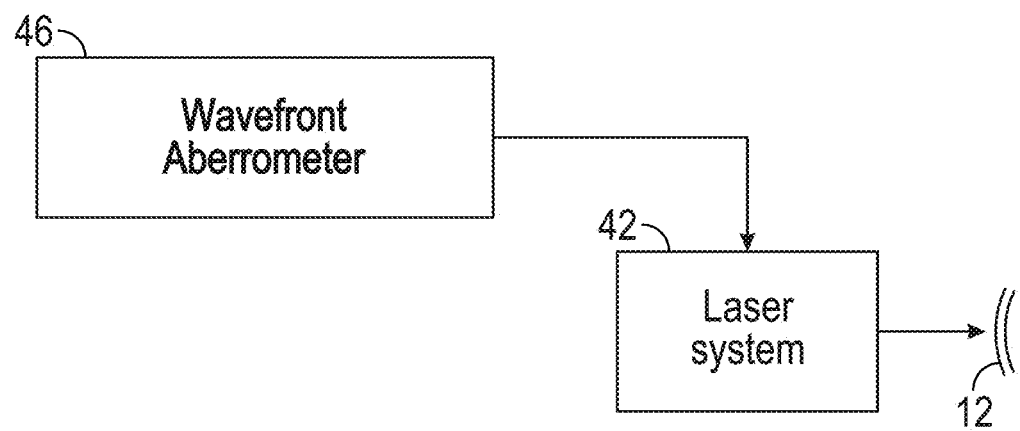
FIG. 2B is another embodiment of a prior art corneal laser ablation system.
Figure 3:
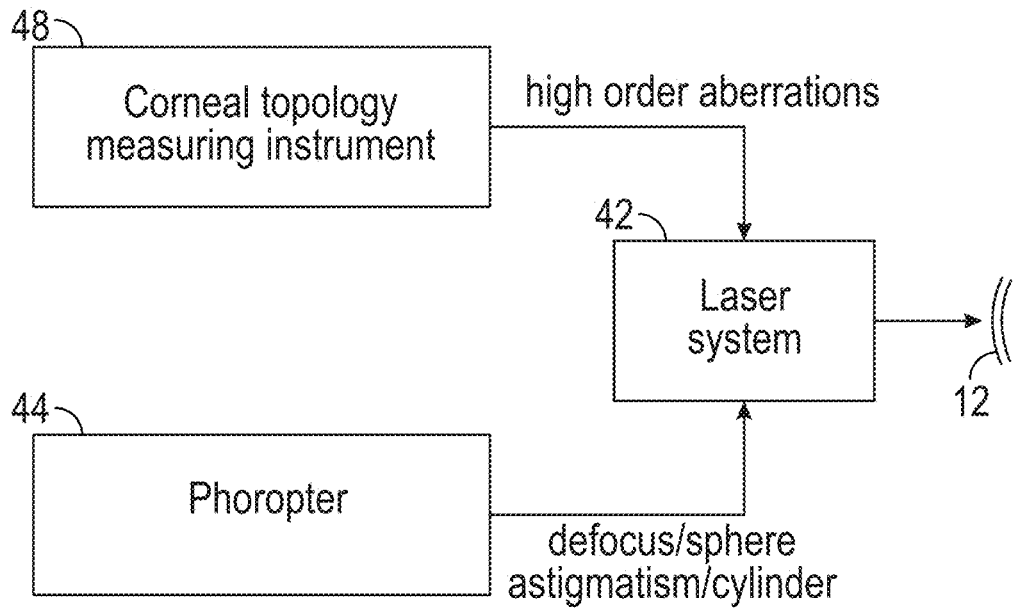
FIG. 3 is a block diagram of a prior art topology guided corneal laser ablation system.

Referring now to FIG. 3, for topographic guided ablation, rather than using a wavefront aberrometer such as shown in FIG. 2B, a corneal topology measuring instrument 46 is utilized. Corneal topology measuring instruments 46 are configured to generate high resolution elevation maps of the surface of the cornea 12. One technique for generating these maps utilizes Placido rings. With this method of topography generation, a series of concentric rings of illumination are reflected off the anterior corneal surface. The characteristics of the light reflected from the anterior surface of the cornea at different locations on the cornea will be dependent on its local curvature and surface features. The reflected light is analyzed and used to create a surface topology map of the corneal surface. Such maps can be very high resolution, and may map the elevation of many thousands of points in a corneal area of a few millimeters diameter. Refractive power maps that characterize the refractive power of the anterior cornea surface at different locations on the corneal surface may also be generated from the gathered Placido ring data. The WaveLight Topolyzer VARIO from Alcon is one example of a commercially available corneal topology measuring instrument that uses a Placido ring illumination and analysis technique. Another method of acquiring corneal topology is known as a Scheimpflug imaging system. This technique acquires images of slices of the eye at different angles. A Scheimpflug camera may acquire a variety of structural information regarding the anterior chamber of the eye with these slice images. This information may include high resolution elevation data for the anterior corneal surface.

Once the topography of the anterior surface of the cornea is defined, this information may be used to design a laser ablation profile for vision correction. A commercially available treatment system comprising a corneal topography instrument, laser ablation profile generator, and ablation laser for topographic guided ablation treatment is the WaveLight Contoura system from Alcon. The Contoura system combines a WaveLight Topolyzer VARIO and an excimer laser system (e.g. WaveLight EX500 or Alegretto Wave Eye-Q) incorporating computational software for generating topological map measurements and converting these into laser ablation profiles for treatment. With the Contoura system, the actual surface contour of the cornea is measured, and this data is used to derive a best fit model of the anterior surface shape of the cornea. This system provides low order refraction measurements based on the model including astigmatism, as well as a detailed map of the anterior surface of the cornea that includes measurements showing where the corneal topology deviates from the best fit model. The areas of deviation of the corneal surface from the best fit model may be referred to as high order aberrations of the cornea surface (which may, along with the low order characteristics of the model, be characterized by the coefficients of Zernike polynomials if desired). The corneal contour data may be derived by measurement and analysis of the cornea with the WaveLight Topolyzer VARIO cornea mapping device and Wavelight Refractive Suite of software. In some implementations, topographic guided ablation may perform two different "layers" of correction. The first layer is the HOA (higher order aberration) removal layer to remove the natural biological aberrations found in the cornea. The second, the refractive correction layer, treats sphere and astigmatism.

A fundamental difference between wavefront aberrometry and corneal topography is that wavefront aberrometry provides information on the combined optical properties of the eye as a whole (e.g. including the anterior corneal surface, the posterior corneal surface, the lens, etc.), whereas corneal topography provides information regarding the surface shape of the anterior surface of the cornea without measuring the optical characteristics of other optical elements of the eye. Perhaps in part because of this specificity of corneal topographic measurements and the fact that manifest refraction has traditionally been considered to be the "gold standard" for measurement of true low order refractive error, corneal topography based measurements of keratometry parameters such as sphere and astigmatism have been essentially ignored in designing laser ablation profiles in topographic guided ablation procedures.

For example, as illustrated in FIG. 3, a measurement of manifest refraction (cycloplegic or not cyclopleged) of the patient may still be performed to get traditional manifest sphere and cylinder correction values, with, for example, a phoropter 44. When a laser ablation profile is created, the layer which is intended to reduce or eliminate high order aberrations is based on the measured high order corneal surface aberrations obtained from the corneal topology measuring instrument 46. The lower order refraction correcting laser ablation layer is based on the manifest refraction sphere and cylinder correction values as determined with the phoropter and subjective patient input (See, for example, *Visual Outcomes After LASIK Using Topography-Guided vs Wavefront-Guided Customized Ablation Systems*, Journal of Refractive Surgery, Vol. 32, No. 11, 2016).

The inventor has observed that the astigmatism determined by the corneal topology measuring instrument may be markedly different from the manifest astigmatism hand measured by a clinician with cooperation from the patient. This situation has been poorly handled to date because the effects of higher order corneal aberrations on lower order corneal astigmatism has until now been poorly understood. If the actual corneal astigmatism from direct topographical measurement differed from the manifest astigmatism, it was usually considered to be due to lenticular astigmatism via a process of exclusion. Thus, Contoura topology guided ablation treatments have been performed using the manifest/cycloplegic manifest refraction (considered herein to be essentially the same—a clinician hand measured refraction such as with a phoropter), which has often been the endpoint for refractive correction, no matter the modality of correction.

New treatment systems and methods were developed by the inventor by examining patients that had a significant difference between manifest astigmatism and Contoura measured astigmatism using topological corneal surface data in an effort to delineate the reasons for induction, modification, and reduction of astigmatism by corneal surface aberrations. A hypothesis is that the higher order aberrations were directly modifying the lower order astigmatism in such a way as the combination of the distortion of the two necessitated the cortical processing to pick a point of "least confusion," resulting in a manifest refraction that was often significantly different from the Contoura measured astigmatism in power, axis, or both.

To address this issue, the inventor has developed the "LYRA" protocol. LYRA is an acronym for Layer Yoked Reduction of Astigmatism. This is a recognition of the fact that the high order aberration removal layer is linked to the refraction correction layer. In one implementation, the protocol is as follows:

1. Enter the manifest refraction into Contoura system during pre-surgical planning
2. Zero out the astigmatism and sphere to see the ablation pattern for the Aberration Correction Layer.
3. Use directly measured actual corneal astigmatism and axis (e.g. measured from the WaveLight Topolyzer VARIO cornea mapping device and Wavelight Refractive Suite of software for example rather than patient manifest astigmatism and axis) for the astigmatism correction. The ablation map at this point should be similar to the Pentacam anterior elevation map. This will assist understanding the ablation when there is a significant discrepancy between manifest vs. measured astigmatic power and axis.
4. The sphere is now used for defocus correction after adjustment for the spherical equivalent of the change in astigmatism.

It will be appreciated that not all steps of the LYRA protocol as described above are necessary to implement embodiments of the invention.

Figure 4:
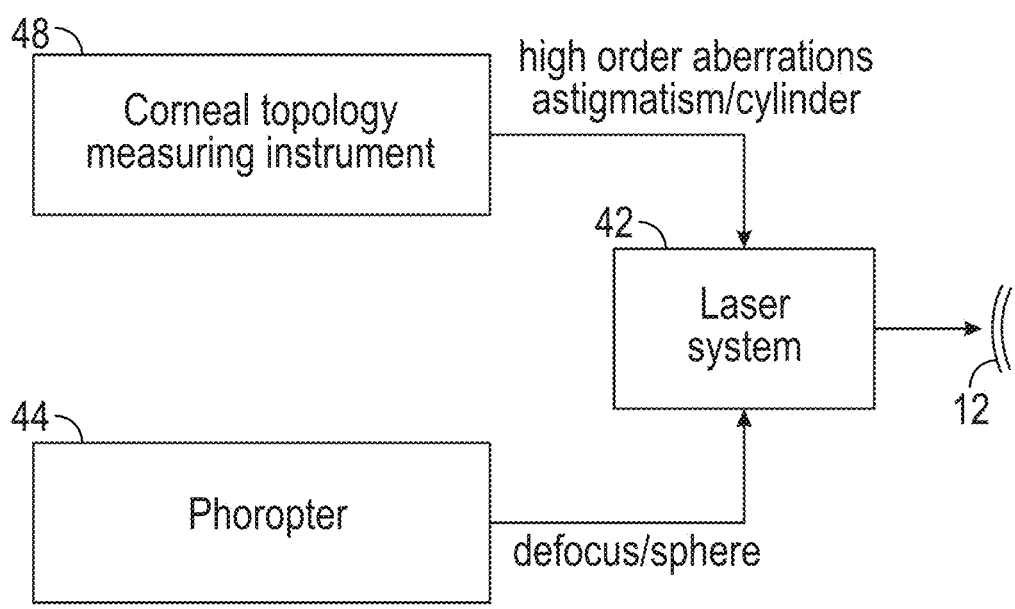
FIG. 4 is a block diagram of an implementation of a topology guided corneal laser ablation system according to some implementations of the invention.
Figure 5:
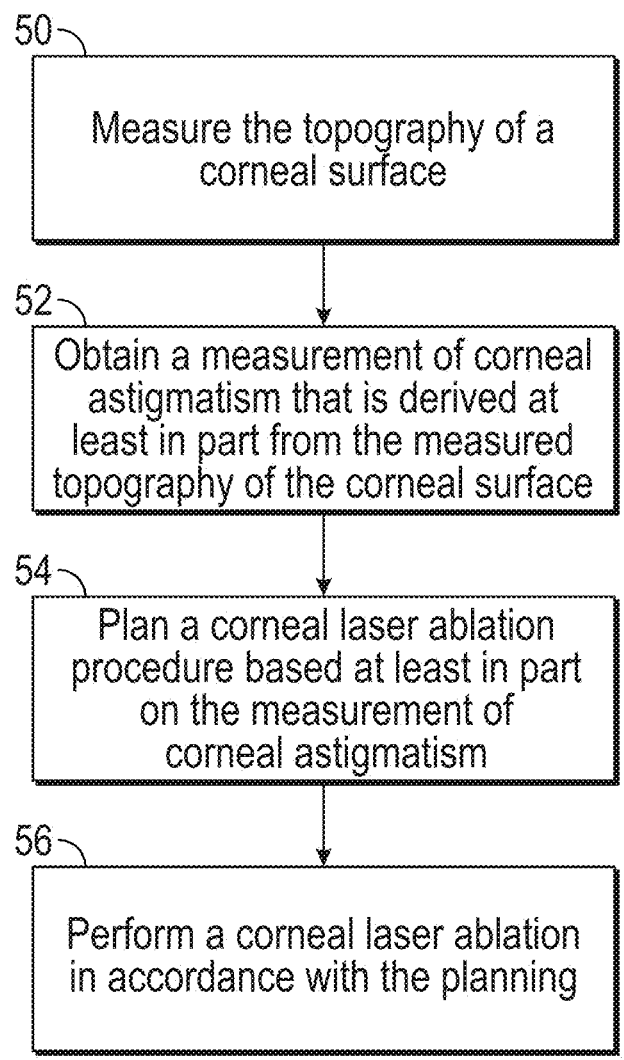
FIG. 5 is a flow chart of a topology guided corneal laser ablation method that may be used with the system of FIG. 4.

A system suitable for implementing some embodiments of a laser ablation correction method is illustrated in FIG. 4 and a flowchart of an example method is illustrated in FIG. 5. The system of FIG. 4 includes a corneal topology measuring instrument 46 as described above, and also a phoropter 44 for measuring manifest refraction. Also similar to FIG. 3, high order aberration measurements from the corneal topology measuring instrument 46 are used to configure the laser system 12 with an ablation profile to ablate at least some high order aberrations from the cornea. In the implementation of FIG. 4, however, the astigmatism information used to configure the laser system for ablation is the astigmatism derived from the topological measurements, not from the manifest astigmatism measured clinically from the patient as in the prior practice illustrated in FIG. 3. The sphere correction used to configure the laser system 12 with an ablation profile may still come from the manifest sphere correction in this implementation. As will be shown further below, ablating in accordance with topographically measured corneal astigmatism instead of the patient's own subjective experience of astigmatism produces better outcomes for topographic guided ablation procedures.

Referring now to FIG. 5, a method according to some embodiments begins with measuring the topography of a corneal surface at block 50. From the corneal topography measurement, a measurement of corneal astigmatism is derived at block 52. At block 54, a corneal laser ablation procedure is planned based at least in part on the corneal astigmatism measurement derived from the topographic data. At block 56, a corneal laser ablation procedure is performed in accordance with the plan. In conjunction with these steps, and as indicated in FIG. 4, the planning and performance may include laser ablation correction derived at least in part from the corneal topographic data for high order aberration removal or reduction. Sphere correction can be planned and performed based on manifest refraction measurements.

PATIENTS AND METHODS

Aberration correction was visualized on the treatment planning page of a Contoura topographic guided ablation system by zeroing out the refraction, and displaying Contoura correction of the aberration. The change of shape to the central cornea was determined using this method, and comparison against the manifest refraction astigmatism and axis was performed. The examination of a large number of eyes resulted in 6 categories where manifest astigmatism was different than measured corneal astigmatism. Those categories are listed below.

All patients were analyzed using the Topolyzer Vario, and all patients had correction by one surgeon (MM) at one center using the Wavelight EX500 system with Contoura and the WaveNet server. During Contoura Planning, excellent topographic image capture with the Topolyzer Vario is desirable, generally at least 4 high quality images, and preferably as many as 8 for processing by Contoura. Mean Average Deviation (MAD) of the astigmatic axis of ≤1 degree was required in the scan group sent to Contoura for processing. The Q value was left unchanged.

As part of this analysis, patients had cyclopleged manifest refractions performed to rule out the existence of lenticular accommodation of astigmatism. All cases below have a pre-op topography, post-op topography, and ablation pattern to illustrate the type of pre-op aberration. The aberration ablation pattern was obtained by the method described above, with laser ablation HOA and astigmatism corrections derived from the topographic data, not manifest refraction measurements.

Figure 6A:
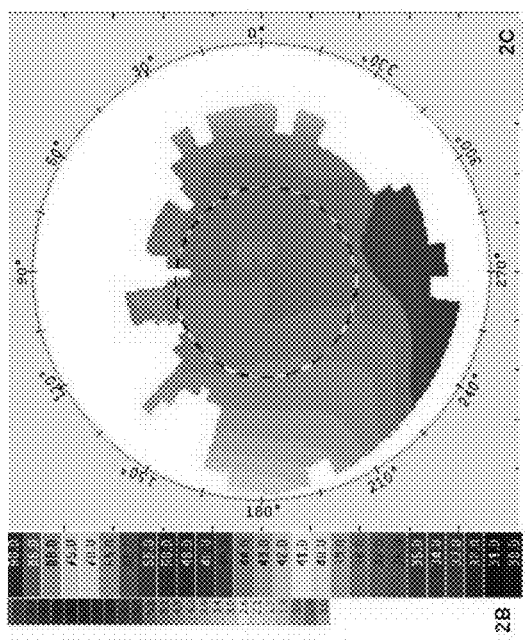
FIGS. 6A through 6E are displays of corneal properties for eyes treated in accordance with certain example embodiments.
Figure 6A:
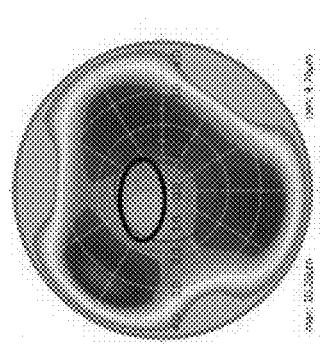
Figure 6A:
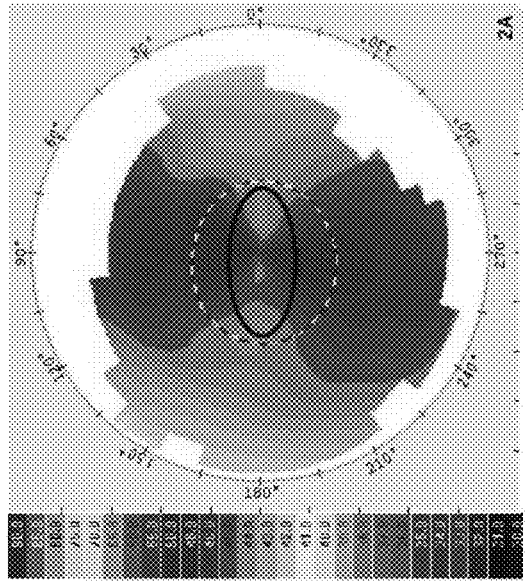

Case 1: Corneal Aberration Induction of Manifest Astigmatism—FIG. 6A

Pre-op Manifest Refraction: −1.00, −2.75×8 with BCVA of 20/20

Pre-op Auto-refraction: −0.50, −2.50×171

Measured Contoura correction: −1.40, −2.00×1

Post-op refraction and vision at 3 months: plano; 20/15

In this case, the higher order aberration creates an oval that adds to the lower order astigmatism oval, increasing the manifest astigmatism. When the HOA is treated, the amount of astigmatism to correct is decreased as demonstrated by the Contoura Measured Correction and post-operative result.

Figure 6B:
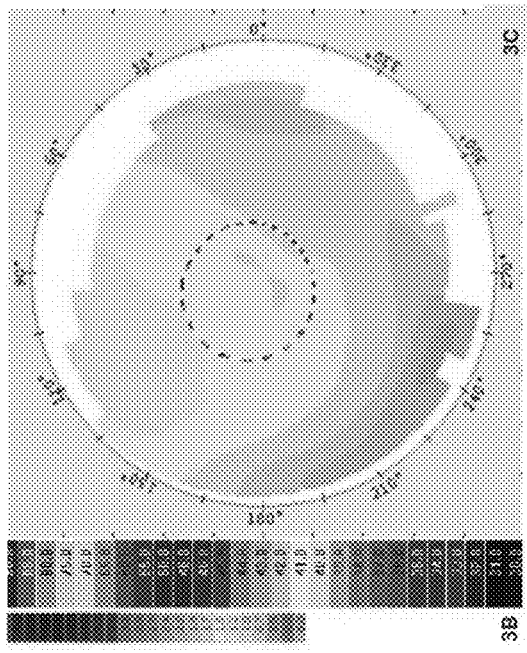
Figure 6B:
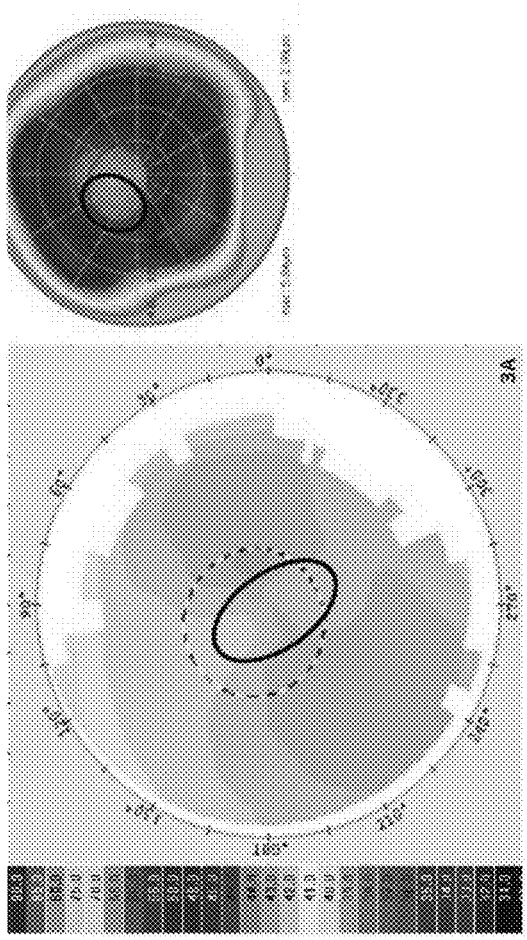

Case 2: Corneal Aberration Cancellation of Manifest Astigmatism—FIG. 6B

Pre-op Manifest Refraction: −1.50 with BCVA of 20/20

Pre-op Auto-refraction: −2.00

Measured Contoura correction: −1.12, −0.77×121

Post-op refraction and vision at 1 week: plano; 20/15

This particular patient had their entire lower order astigmatism completely cancelled out by the higher order aberration resulting in a manifest refraction with no astigmatism (no astigmatism on the auto-refraction also). The oval caused by the lower order astigmatism is oblique (oblique astigmatism has only been seen rarely by us), as is the ovalization created by the HOAs, and the two ovals completely cancel each other out during manifest refraction. Removing the higher order aberration reveals the lower order astigmatism underneath, which can be recognized as "bowtie" astigmatism on the cornea.

Cases 1 and 2 essentially demonstrate either cancellation or induction of astigmatism with ovalization created by the HOAs that is either on the same axis or perpendicular to the oval created by the lower order astigmatism.

Figure 6C:
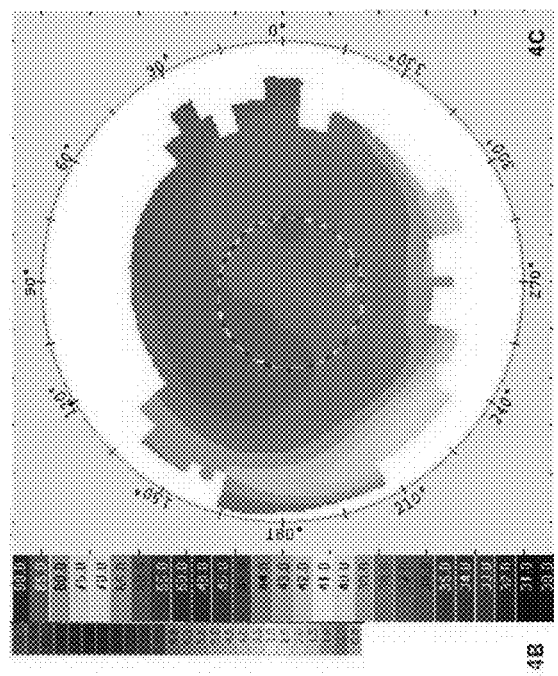
Figure 6C:
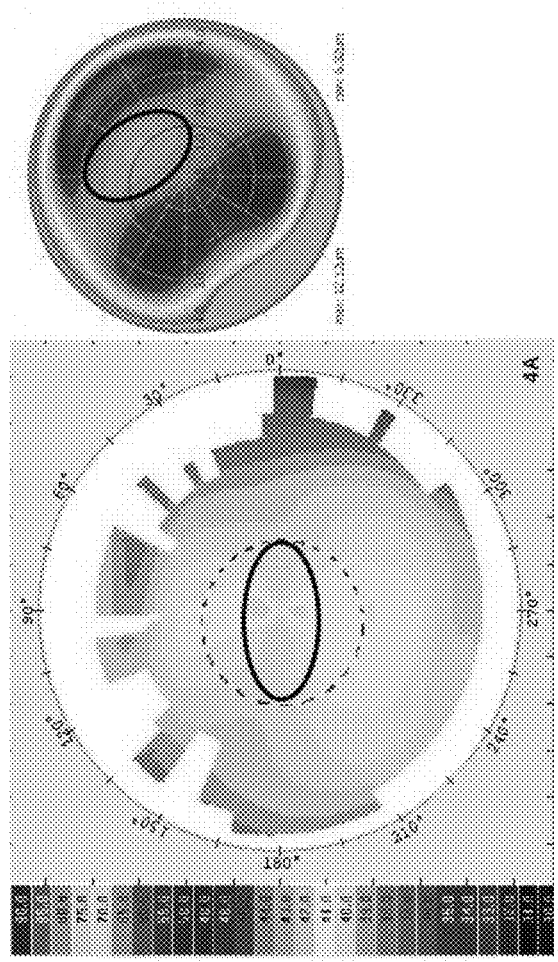

Case 3: Astigmatism Aberration Cancellation via Oblique Aberration and Cerebral Processing—FIG. 6C Pre-op Manifest Refraction: −2.75 with BCVA of 20/20

Pre-op Auto-refraction: −3.75, −0.25×150

Measured Contoura correction: −2.40, −0.77×1

Post-op refraction and vision at 1 month: −0.25; 20/15

This patient shows with-the-rule astigmatism on topography, but has a manifest refraction and auto-refraction that essentially shows no astigmatism. The ablation pattern shows correction of trefoil, but the oval created is not along the axis expected to cancel out the corneal lower order astigmatism. It is at an oblique angle. The other eye of this patient had a similar with-the-rule astigmatism on topography, similar lack of astigmatism of manifest and auto-refraction, but the aberration oval was perpendicular to the lower order astigmatism and clearly cancelled it out. This one is at an oblique angle, so it appears that somehow the patient's cerebral processing is working similarly to the other eye, but somehow still cancelling out the astigmatism with an oblique aberration. It is difficult to see how even examining this aberration in 3 dimensions would somehow create an ovalization that was directly perpendicular to the oval created by the lower order "bowtie" astigmatism. The result of Contoura Measured correction resulted in 20/15 vision with all astigmatism removed in both eyes.

Case number 3 demonstrated a different sort of issue, where the oval shape created by the aberration was oblique to the axis of the corneal astigmatism, yet seemed to fully cancel it out. This is a case we cannot fully explain via corneal factors. This patient also did not display any astigmatism on cyclopeged refraction, or auto-refraction. Although it is possible that the oval created centrally is not as oblique as the overall shape of the trefoil aberration in his cornea, we think just as likely it may be that cerebral processing is involved. This patient's other eye had a textbook cancellation of with the rule astigmatism by corneal aberration. It may very well be that there was partial compensation of the astigmatism in case 3 by the aberration, and partial compensation of the corneal astigmatism via cerebral processing. We know that manifest refraction is based simply on the point of least confusion of vision, and we know that what we "see" is actually subject to cerebral processing.

This particular case was an anomaly, and the only one that the author has seen like this, where it seems cerebral processing somehow allowed an oblique aberration to cancel out a regular with-the-rule astigmatism. In this case, it is difficult to see even how examining this aberration in 3 dimensions would somehow create an ovalization that was directly perpendicular to the oval created by the lower order "bowtie" astigmatism. In Case 5, we also demonstrate a case where an oblique aberration appears to cancel out a with-the-rule lower order astigmatism. In that case, an oblique astigmatism is created on manifest refraction. In this case, there is no oblique astigmatism on manifest refraction, just a complete cancellation of with-the-rule astigmatism. Cerebral processing is responsible for the below picture, where the lines don't look parallel but actually are (FIG. 5). This type of simple drawing is an example of how cerebral processing can be used to alter how we "see" things.

Figure 6D:
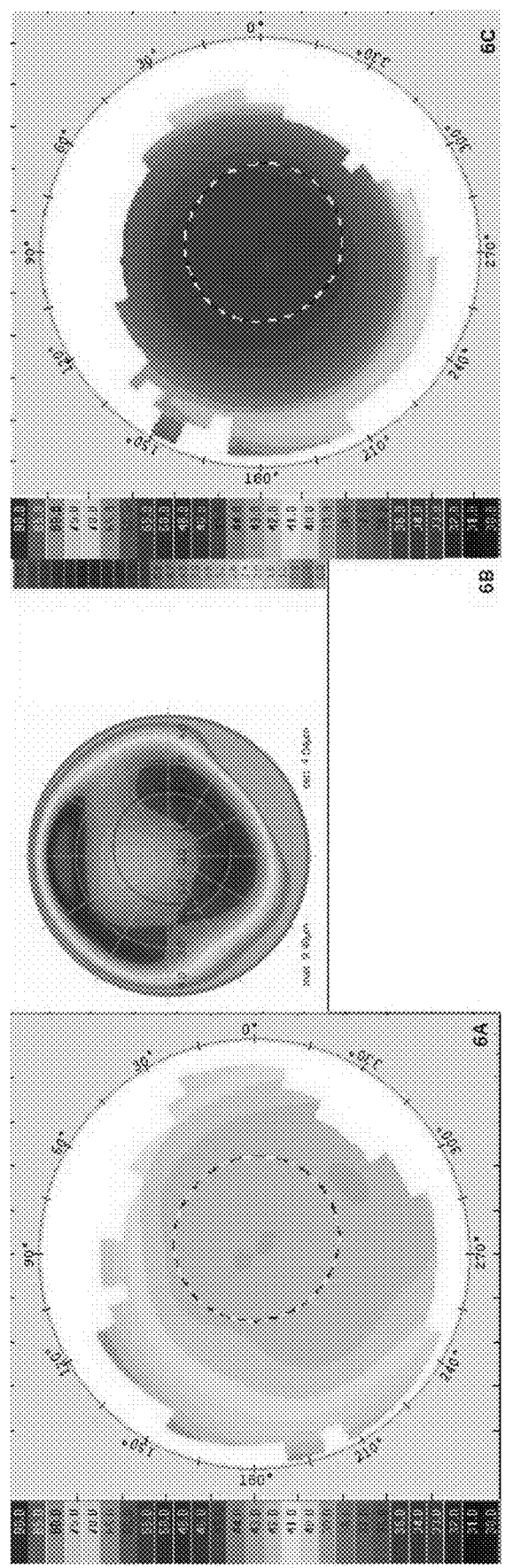

Case 4: Aberration Induction of Astigmatism with Dilation of the Pupil—FIG. 6D

Pre-op Manifest Refraction: −7.75, −1.00×75 with BCVA of 20/20

Pre-op Auto-refraction: −8.00, −0.75×75

Measured Contoura correction: −8.00, −0.07×121

Post-op refraction and vision at 1 month: plano; 20/15

This patient has coma directly adjacent to the pupil, causing manifest refraction and auto-refraction of astigmatism. The presence of this "high spot" peri-pupillary coma creates a localized distortion and astigmatism on manifest refraction. Removal of that coma completely eliminates the astigmatism and essentially leaves sphere. The sphere was corrected resulting in a uniform looking cornea and 20/15 vision.

Case number 4 demonstrates how coma peripheral to the pupil can result in incorrect measurement of astigmatism in a dark room with a mydriatic pupil, or during cyclopleged refraction. Correction of this astigmatism results would lead to an incorrect result, as there is no actual astigmatism, but a localized distortion created by the "high spot" of the peri-pupillary coma. Such a patient may have decreased or no manifest astigmatism with a meiotic pupil, as the pupil may close enough to decrease or eliminate the distortion created by the coma. Removal of the coma results in a cornea that has no astigmatism on either manifest or cyclopleged refraction. Not only can the coma cause a manifest astigmatism, but it can also change the axis of astigmatism of an actual lower order corneal astigmatism, resulting in an incorrect treatment. This particular patient had astigmatism at an oblique axis on manifest, cyclopleged manifest, and also auto-refraction. Contoura Measured showed no astigmatism at all, supported by the fact that no lower order astigmatism is noted on the pre-op topography. Similar examples can be demonstrated with corneal keratoconus patients the predominating aberration is coma (where except in the case of central keratoconus).

Figure 6E:
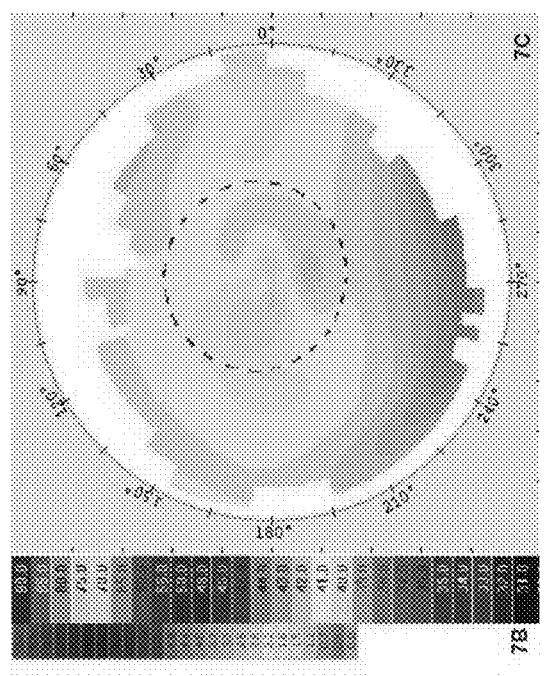
Figure 6E:
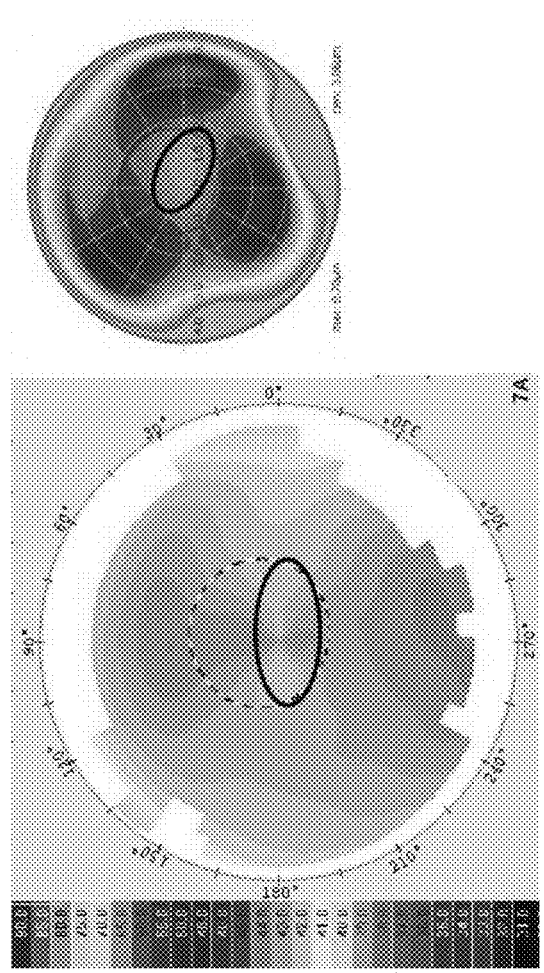

Case 5: Oblique Manifest Astigmatism Induced by Corneal Aberration—FIG. 6E

Pre-op Manifest Refraction: −2.50, −0.50×155 with BCVA of 20/20

Pre-op Auto-refraction: −2.75, −0.50×142

Measured Contoura correction: −2.00, −1.50×1

Post-op refraction and vision at 1 month: plano; 20/15

This patient has an obvious with-the-rule "bowtie" astigmatism, yet both manifest and auto-refraction show an oblique astigmatism of a much smaller magnitude. In this particular case the trefoil is creating an oval that is at an oblique angle cancelling out the with-the-rule astigmatism and also creating an oblique astigmatism. Removing the aberration results in 1.50 D of with-the-rule astigmatism. The topography shows signs of the epithelium still becoming uniform from epithelial molding to the aberration. This will likely smooth out 3 to 6 months post procedure.

Case number 5 demonstrates how an oblique aberration oval changes the with-the-rule astigmatism noted on topography to an oblique manifest astigmatism. This case shows how the interaction between lower and higher order astigmatism can also end up with an oblique axis of astigmatism being created. In this particular case not only does the oblique oval created by the trefoil cancel out the with-the-rule astigmatism, but it creates a tangential astigmatism at an oblique axis.

After observing the interactions between higher and lower order astigmatism over many Contoura with LYRA Protocol corrections, some observations have been made. The vast majority of lower order astigmatism is actually either with- or against-the-rule, with an axis of astigmatism usually within +/−15 degrees of the 90 degree and 180 degree axes. It appears that oblique manifest astigmatism seems to be mainly caused by either an oblique oval created by an aberration, or by peri-pupillary coma that affects the mydriatic and cylopleged manifest measurements.

Case 6: Pure Lenticular Astigmatism

This case has a wavefront measured astigmatism of −3.5 D at 84 degrees, a manifest astigmatism of −1.75 D at 90 degrees, and a Contoura Measured astigmatism of −1.49 D at 81 degrees. The Contoura Measured astigmatism is very close to the manifest astigmatism, while the wavefront shows a much higher amount of measured astigmatism. In this case, the corneal aberration is cancelling out astigmatism that can only be coming from the lens, and treating the Contoura Measured will reveal astigmatism from the lens. The diagnosis of such a case is best done with wavefront measurement, and treatment of residual astigmatism can either be done with wavefront-guided or likely even wavefront-optimized correction. If the surgeon elects to treat, they must inform the patient of the need for re-treatment if cataract surgery is ever necessary.

Case number 6 demonstrates pure lenticular astigmatism. This patient has minimal lower or higher order corneal astigmatism, but has a manifest refraction showing astigmatism. This patient has not had laser vision correction performed. It appears that lenticular astigmatism may be much less common than has been estimated.

An understanding of how higher order aberrations (HOAs) affect lower order astigmatism came about as an attempt to understand why using the topographically derived astigmatism rather than the manifest astigmatism is effective. Different theories were examined, but the underlying fact was that using the topographically measured astigmatism resulted in good vision even when the manifest astigmatism/axis differed markedly from the topographically measured astigmatism/axis. Over time, examining the HOA pattern of patients in relation to their lower order astigmatism, and the changes from manifest refraction to Contoura Measured led to an understanding of how the HOA's were interacting with the lower order astigmatism.

The theory that lenticular accommodation of the cornea may exist to explain some of the differences in between manifest and measured refraction was considered. This would be where the lens is capable of accommodating in such a way as to correct or even cause astigmatism. This has never been proven to exist, but was a theory that was considered. Cycloplegia would actually provide a different astigmatism refraction that would be closer to or equivalent to the topographically measured astigmatism if lenticular accommodation of astigmatism was present. Unfortunately, in no cases that the author examined was this demonstrated, and all patients considered for this analysis had cyclopleged refractions to rule out any accommodative aspect. It appears that peripheral or central higher order aberrations create an ovalization in the central cornea (within the mesopic pupil), resulting in a deformed central ray of light forming a lower order astigmatism. Therefore, the manifest refraction is a result of the oval shapes created by lower order and higher order astigmatism and its resulting central ray of light interaction. Corneal lower order astigmatism essentially creates an oval shape in the center of the cornea, as shown below in the diagrams. Corneal aberrations such as trefoil and quadrafoil can also create an oval shape to the central cornea, and depending on how the two ovals of higher order and lower order aberration line up, it will either increase or decrease the manifest measurement of astigmatism.

It also appears that the central ray of light forms the main part of vision, and the refraction requested by the patient (e.g. the manifest refraction) achieves the best possible correction that minimizes cerebral confusion via the addition of spherical or astigmatism glass correction. This visual impression of the patient is widely determined by the shape formed by low and high order aberration that pass the central portion of the cornea and form the related focusing at the retinal level. Aberrations located at the periphery will influence the overall quality of vision. Spherical aberration for example, is understood to affect night vision. It adds or reduces the amount of refraction, (depending on the orientation of the spherical aberration) when the pupil widens. The dilated pupil allows the pre-existent higher order aberration to become dominant and change the focus quality at the retinal level. The inventor has demonstrated that high order aberrations can also affect the visual impression of the patient. Furthermore, the auto-refractometer might not be able to detect the difference between higher order aberration and low order, since it measures only the central 2 mm of the cornea and therefore the ray of light deformed by the lower and higher order aberrations.

What the inventor has observed across the examination of many patients is that the majority of higher order aberrations are trefoil, with a lesser amount of quadrafoil, and coma. When the aberration is examined using topographic measurement derived elevation and power data, it was possible in some cases to see the oval created by the aberration and how it impacted the actual corneal astigmatism. There appear to exist many cases with a completely different topographically measured astigmatism vs. manifest. The inventor surmises that it is cerebral processing that compensates for the distortion caused by HOA's. The cerebral cortex must interpolate information where it becomes distorted by an HOA, and removal of that HOA would remove the need for that interpolation. Although there has been some conjecture in the past that some aberrations may be good, i.e. as in fighter pilots that have 20/10 vision and HOA's, the author believes that the high resolution for the 20/10 vision comes from a high density of photoreceptors in the retina in these individuals, and a fighter pilot's or baseball player's high capabilities in dynamic vision testing is due to rapid cerebral interpolation to compensate for distortion created by HOA's. If this is the case, then removal of the HOA's on a person who is already 20/10 would result not in better Snellen visual acuity (which would be limited by retinal photoreceptor density in the macula), but in faster response times as cerebral processing/interpolation would no longer be necessary. Furthermore, the ability to clearly see the edges of objects would allow for faster "locking in" by the brain for dynamic motion, likely resulting in better response time to a 95 mile per hour fastball or a fast flying opposing fighter which require responses in the milliseconds. The inventor postulates that there is no such thing as a "good" aberration, but essentially all aberrations are bad and require cerebral processing to compensate for them. Treating these HOA's to make a more uniform cornea will simply allow a clear path of light that will not need to be compensated for.

It may also be mentioned that too much emphasis can be placed on the Snellen visual acuity as a measure of vision performance. In some cases, 20/15 patients that are not happy, some patients are treated for halos who are clearly 20/15 Snellen but have 0.5D of astigmatism and are dissatisfied with their night vision. Treating that residual astigmatism significantly improves the night time vision and decreases halos. In our experience, a patient who is 20/20 without halos is happier than a 20/15 with. An eye with 20/15 or 20/10 vision after laser correction means that the treatment allowed the retina to more fully achieve its resolution, but it does not guarantee that residual aberrations of the cornea will result in a patient who is completely happy.

For purposes of visualization, with the rule astigmatism essentially results in a horizontally oval cornea. If the aberration also creates an oval that is horizontal, the manifest astigmatism will be greater than the corneal astigmatism. If the aberration creates a vertical oval on the same type of cornea, the manifest astigmatism will be cancelled out or less than the corneal astigmatism. Depending on the axes of the two "ovals" the manifest and topographically measured axis may be significantly different also.

Manifest refraction has inherent technical and subjective limitations when determining the precise value for cylinder power and axis. Manifest refraction requires subjective input by the patient, and is based on the point of least confusion in the patient's vision. It is subject to technical and subjective errors. Furthermore, topographic guided ablation using manifest refraction correction does not take into account the effect on astigmatism/astigmatism axis when higher order aberrations are removed. This makes the situation even more complex, as not only can there be a new abnormal induced astigmatism when correction is done without HOA removal on the wrong manifest axis, but the lower order astigmatism axis can change when the effects of the higher order aberrations are removed. This builds on the new understanding of the interaction of HOAs on refractive astigmatism described above. In fact, removal of the HOAs overwhelmingly resulted in refractive astigmatism that was within 15 degrees of the 90 and 180-degree axes showing that most eyes simply do not have oblique lower order astigmatism. Removal of the HOA often resulted in a different lower order astigmatism and axis, and unless the manifest astigmatism and axis coincide with the topographically measured astigmatism and axis (an uncommon occurrence in our experience), correction with the Manifest Refraction will not only be incorrect, but will also induce a new abnormal astigmatism which can be visualized on topography.

The correct use of topographic guided ablation as described above creates more uniform corneas, and it also allows better vision. No other vision correction modality (save a properly fitting RGP lens), whether glasses, contacts, normal or wavefront guided LASIK, SMILE, ICL, or IOLs are able to correction vision this way. This would be the first vision correction modality, again save perhaps RGP lens, that is not an equivalent, but potentially better. This in itself would be a revolution in laser correction, as for the first time we would have a procedure that could allow the full potential of the eye to be reached, and actually allow the refractive surgeon to tell the patient that topographically guided laser ablation with the methods and systems described above has the potential to achieve better vision than virtually any other modality of vision correction. Although lens flaws and posterior corneal astigmatism that may be present, it appears they play a smaller role than originally thought. If these latter factors are not affecting the vision significantly, and topographically guided laser ablation can produce a substantially smooth and spherical anterior corneal surface, then the major limitation on vision clarity, acuity, and resolution would be retinal neuro-receptor density.

It has also been found that although a change in Q value from the ablation would theoretically induce some spherical aberration, experience has demonstrated that this is small enough in primary topographic guided ablation corrections to be generally ignored in the above procedures. Change in spherical aberration by the Q change may be addressed in retreatments, through the equalization of the C4 and C12 Zernike polynomials. As this document is mainly concerned with demonstrating that utilizing topographically measured astigmatism power and axis is effective, we will not address retreatments in detail here.

A retrospective analysis of the first 50 primary LASIK corrections of 26 patients performed by the inventor within the FDA indications of myopia up to −8.00 D with astigmatism no more than −3.00 D was undertaken. All surgeries were performed by the inventor at one center in San Diego, Calif. using a Wavelight EX500 with Contoura and the Topolyzer Vario. All LASIK flaps were made with the Moria M2 Microkeratome with 110 micron calibrated blades from Microspecialties. All surgical planning was done using the Wavenet Server and the Contoura planning system using the above described topographic guided protocols. The topographic measured astigmatism and axis were obtained from the Surgical Planning page in the Contoura planning software.

This study included 50 eyes from 26 patients of which 10 were male and 16 were female. Patient ages ranged from 19 to 62 years, with an average age of 31.65 years. Specific attention was paid to obtaining high quality reproducible scans with the Topolyzer Vario. A patient would have 8-12 scans taken per eye, and at least 4 accurate similar scans with appropriate iris registration and complete data (as indicated by the Topolyzer Vario) were necessary to proceed in surgical planning. If the scans were too variable, or not enough scans with high quality information were taken, the scans were repeated until enough scans to create an accurate, reproducible, consistent picture were obtained. Great care was taken not to induce astigmatism when holding the eyelids open for scans, and blinks were allowed to prevent the corneal surface from desiccation.

Patients were not included if they had prior refractive surgery, could not achieve 20/20 vision pre-operatively, were not within the FDA treatment parameters, had anterior segment abnormalities or findings that could affect the outcome such as keratoconus or corneal ectasia, recurring eye disease such as iritis or herpetic keratitis, severe dry eye, uncontrolled diabetes or hypertension, or were pregnant.

Every eye of the 25 patients (50 eyes) received astigmatism treatment. The average of the absolute value of the deviation of astigmatic power from Manifest to Measured was 0.5462 D (range=0-1.69 D). Average amount of deviation of axis from manifest to topographically measured was 14.94 degrees (range=0-89). Eleven eyes had no astigmatism on manifest refraction, but had astigmatism when topographically measured.

Forty-seven eyes were targeted for plano, 3 were targeted for monovision (−1.25, −1.25, −1.50). Of the 47 targeted for plano, 44 (93.6%) eyes were plano and 1 (3.68%) eye was −0.50 D. The remaining 2 had residual refractive errors of:
 plano, −1.00×93 (Sph. Equiv=0.50)
 +0.50, −1.00×105 (Sph. Equiv=plano)

In the 47 eyes with a target of plano, all (100%) were within a spherical equivalent of +/−0.50. In the 3 eyes that were corrected for monovision, one eye overcorrected and underwent enhancement of +0.75 D, and one eye with a goal of −1.25 regressed to −1.50, −0.75×150, and the final one had a goal of −1.25 and was corrected without any regression. Therefore, 49 of 50 (96%) eyes were corrected within a spherical equivalent of +/−)0.50 D, and one eye off by 0.75 D of sphere. Only 2 eyes had residual astigmatism, thus 48 out of 50 Eyes (96%) had full astigmatic correction. 1 eye had regression with an astigmatic component.

One patient had two eyes with significant residual error: pl, −1.00×93 OD and +0.50, −1.00×105 OD. This patient had an auto-refraction and manifest astigmatism of −0.75 D OD, no astigmatism on auto-refraction or manifest refraction OS, and no astigmatism correction in her glasses OU. Her pre-op Contoura Measured astigmatism was 2.55 D OD, and −1.09 D OS. Post-op Contoura analysis demonstrated 0.47 D of astigmatism at one week, and 0.88 D at 3 weeks in OD. We determined pre-operative epithelial compensation of the aberration was responsible for the residual astigmatism, resulting in incomplete measurement of the pre-op aberration (which was trefoil).

Although visual acuity was not a primary goal we present it here for completeness. Of the 47 eyes that had a goal of plano:
 20/10: 3 eyes (6.38%)
 20/15: 38 eyes (80.85%)
 20/20: 47 eyes (100%)

Of the other 3 monovision eyes, distance vision was 20/30, 20/40, 20/70 and reading was J2 or J1. About 81% of the eyes with plano correction were already at 20/15 in this limited study, and 100% of the eyes were 20/20 or better.

Figure 7A:
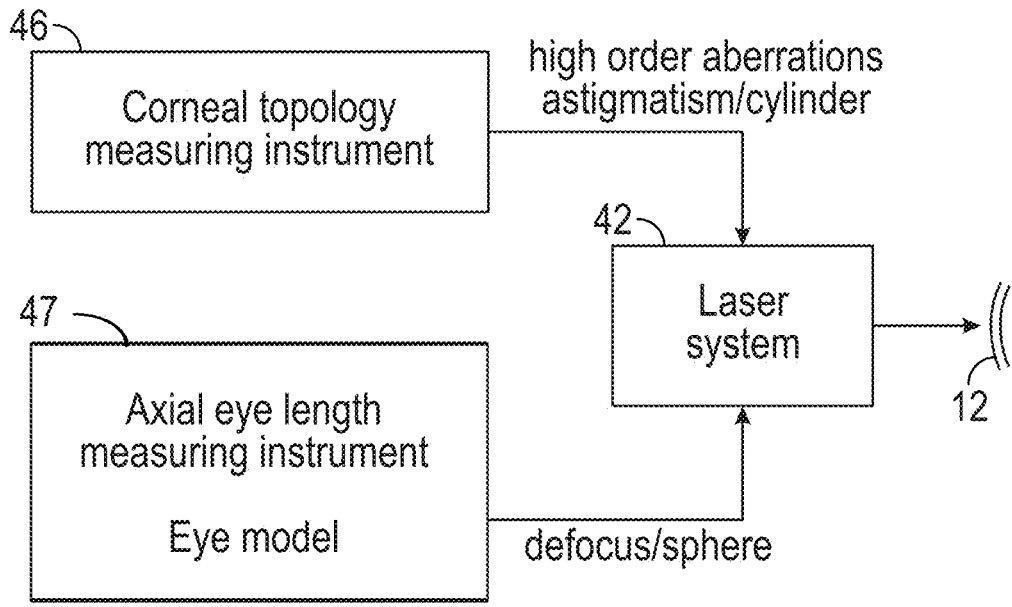
FIGS. 7A and 7B are block diagrams of implementations of topology guided corneal laser ablation systems including other measurement modalities.
Figure 7B:
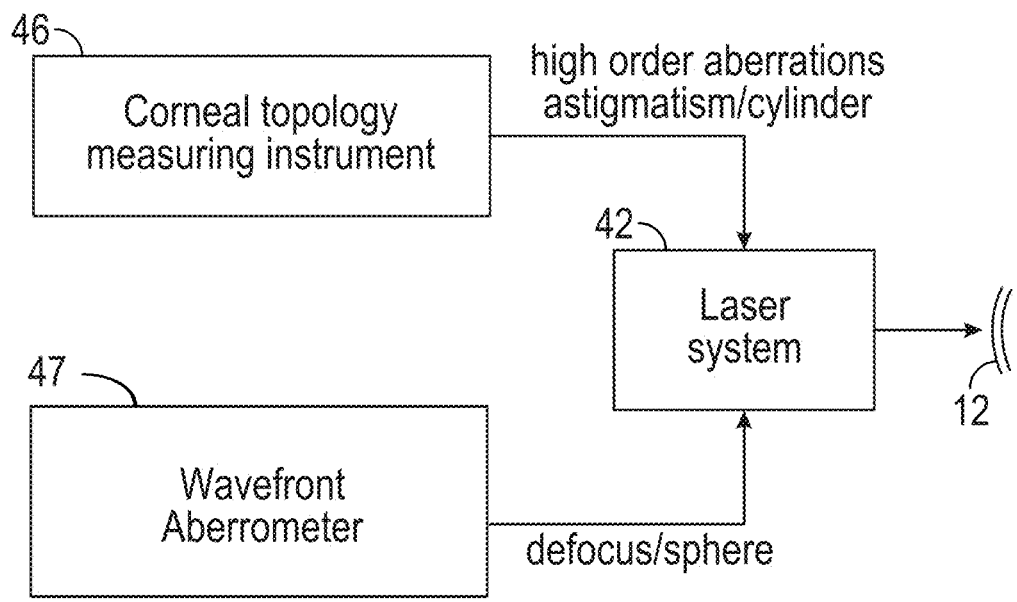

FIGS. 7A and 7B illustrate possible refinements and alternatives to the methods and systems described above. As described in detail above, it has been found especially advantageous to correct HOAs and astigmatism with laser ablation profiles derived from corneal topology measurements. For the defocus/sphere correction, one option is the manifest sphere correction from a phoropter, which was also mentioned above. As another option, obtaining an additional measurement of eye axial length may further reduce or eliminate reliance on manifest refraction measurements. Convenient methods of measuring eye axial length have been developed which may be leveraged to provide this. In fact, instruments for measuring eye axial length (along with other parameters such as anterior corneal curvature, anterior chamber depth and lens thickness) are commercially available and are regularly used when planning IOL implant surgeries. Examples include the Lenstar LS 900 from Haag-Streit Diagnostics and the IOLMaster 500 and 700 from Zeiss. These instruments may use laser interferometry or reflectometry on corneal and retinal reflections of a laser light source to measure eye axial length.

With information on corneal power from the topography measurements and eye axial length from laser interferometry, a semi-custom eye model can be generated, based for example on the Gullstrand eye model or Liou-Brennan eye model, but incorporating some patient specific measurement parameters. For the model, a realistic estimate of lens power can be used. For example, lens power for the model can be assumed to be 18 diopters. From the topographic data and laser ablation plan, the corneal surface contour remaining after correction for HOAs and astigmatism can be determined. A curvature modification to this substantially spherical remaining surface can be computed such that the semi-custom eye model predicts an appropriate focal point on the retina for the whole eye optical system. This modification can be used for planning the spherical component of a correction to be performed with laser ablation in conjunction with topographically derived HOA and astigmatism laser ablation corrections.

In contrast with IOL surgery, procedures for primary refractive correction have not utilized axial eye length as a planning parameter. Given the reliance on manifest refraction measurements, it has not been thought necessary. However, as shown above, manifest refraction is not always the best source of data on which to base a laser ablation treatment. With a measure of axial length and an eye model, spherical corrections can be performed in addition to the HOA and astigmatism corrections described above with little or even no reliance on subjective manifest refraction measurements. It may be noted that the axial eye length measuring instrument 47 and the corneal topology measuring instrument 46 of FIG. 7A can be combined together into a single instrument that can perform the required measurements in a single patient procedure. In fact, the Lenstar LS 900 device mentioned above includes axial eye length measuring capabilities and can be configured to perform Placido ring corneal topography as well, thus combining instruments 46 and 47 of FIG. 7A into one package.

As shown in FIG. 7B, other measurement techniques to implement these novel procedures can be utilized. As another alternative, because both corneal refraction and lens refraction (as well as any other refracting interfaces in the eye) are incorporated into the measurement, wavefront aberrometry can be used to obtain a sphere correction without reference to manifest refraction measurements. Thus, an instrument that combines a corneal topography measuring instrument and a wavefront aberrometer can be a highly suitable device to obtain data for planning a laser ablation in accordance with the principles set forth above. One example of a commercially available device that combines these measurement instruments is the Schwind Peramis from Schwind eye-tech-solutions GmbH. Other refraction measurement devices include autorefractors and retinascopes. These can also be used to obtain a sphere correction value without subjective manifest refraction measurements.

Figure 1B:
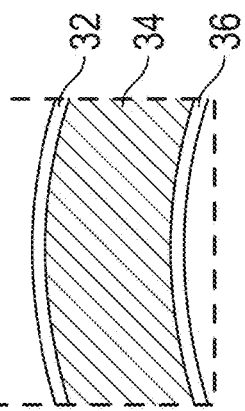
FIG. 1B is a close up view of the cornea of FIG. 1A.
Figure 8:
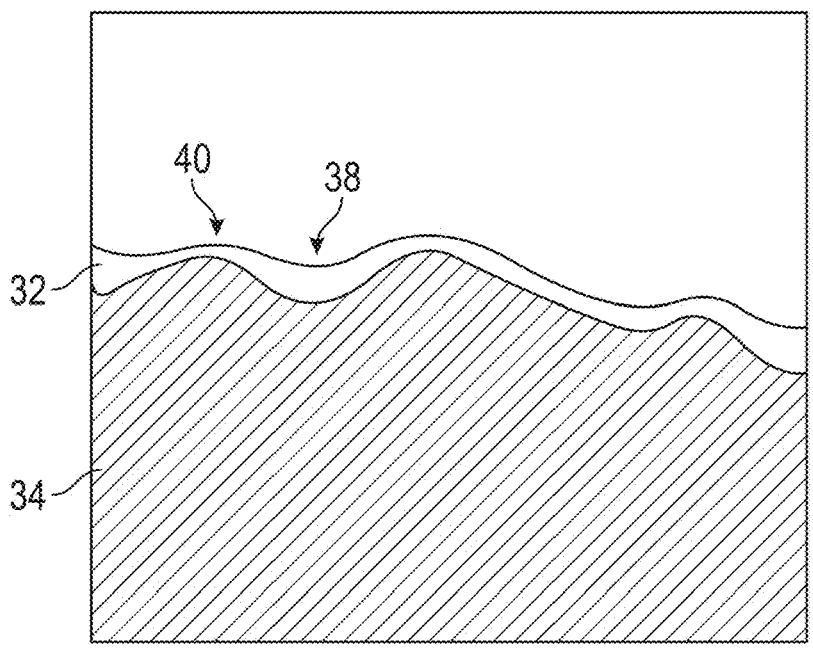
FIG. 8 is a corneal cross section illustrating the anterior corneal epithelium.

Another potential refinement to the above procedures relates to compensating for variations in epithelium thickness over the cornea surface. Referring back to FIG. 1B, corneal surface modification with laser ablation is often performed by peeling back a flap of the epithelium 32 and ablating the stroma 34 directly. The flap is then put back over the ablated area. As shown in FIG. 8 however, the epithelium 32 is not necessarily of constant thickness over the corneal surface. In actuality, as the epithelium covers surface irregularities in the anterior surface of the stroma, it tends to thicken in relatively depressed areas or valleys 38, and become thinner over the peaks 40 of these abberations. Placido ring topographic measurements follow the contour of the tear film covering the epithelial surface, rather than the stroma directly, and this variation in epithelial thickness can lead to errors in the laser ablation pattern generated to perform the topographically based HOA removal layer of laser correction because the epithelium 32 generally smooths out the underlying irregularities of the stroma surface. To reduce these errors, an epithelial thickness map can be created either with optical coherence tomography or very high frequency ultrasound measurements for example. Before generating the laser ablation pattern to be applied to the patient, the epithelial thicknesses can be subtracted from the corneal topography map to get a more accurate assessment of the irregularities in the stroma surface to be ablated during the procedure.

Figure 9:
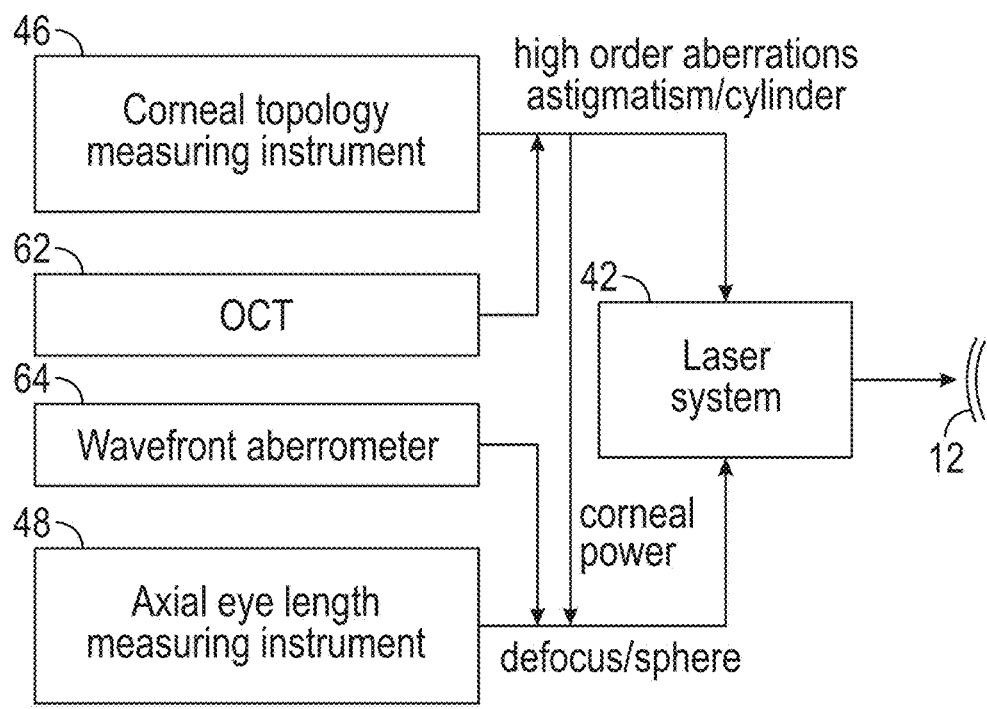
FIG. 9 is a block diagram of another implementation of topology guided corneal laser ablation system including other measurement modalities.

Commercial instruments that measure epithelium thickness are available, for example the iVue and iFusion optical coherence tomography (OCT) products from Optovue. FIG. 9 illustrates an incorporation of this measurement technique to the systems illustrated above.

In the system of FIG. 9, an optical coherence tomography instrument 62 is used to obtain epithelial thickness measurements. These are subtracted from the topographical data obtained by the corneal topology measuring instrument 46 to improve the accuracy of the HOA correction performed by the laser system 12. A wavefront aberrometer or an axial eye length measuring instrument may be used to provide the defocus/sphere correction for generating the laser ablation profile performed by the laser system 12.

In many cases, it may be optimal to collect manifest refraction data, wavefront aberrometer data, and axial eye length data in preparation for a topographic guided laser ablation procedure to be confident that the sphere correction to be used as part of the planning is accurate, rather than rely on a single source for that planning information. As noted above for Case number 6, preoperative wavefront aberration data may also be useful to determine whether a given patient is not a suitable candidate for the procedures described herein due to true lenticular astigmatism. In some cases, it may also be advantageous to correct HOAs and astigmatism initially according to the topographic data as described above, and complete the sphere correction (possibly with spherical aberration correction also) in a retreatment.

Although the present disclosure has been described in terms of certain preferred features, other features of the disclosure including variations in dimensions, configuration and materials will be apparent to those of skill in the art in view of the disclosure herein. In addition, all features detailed in connection with any one aspect herein can be readily adapted for use in other aspects herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

The invention claimed is:

1. A corneal laser ablation system comprising:
   a corneal topography measuring instrument;
   a laser system configured to emit pulsed laser light at one or more wavelengths and configured to control the parameters of laser emission such that the laser output is suitable for controlled ablation of an anterior corneal surface;
   wherein the laser system is configured to control the laser output to ablate at least some high order aberrations from the anterior corneal surface in accordance with topographical measurements of the anterior corneal surface made with the corneal topography measuring instrument;
   wherein the laser system is configured to control the laser output to ablate the anterior corneal surface in a manner that reduces astigmatism of the anterior corneal surface in accordance with a corneal astigmatism derived at least in part from the topographical measurements of the anterior corneal surface made with the corneal topography measuring instrument; and
   wherein the laser system is configured to control the laser output to change a spherical power of the anterior corneal surface in accordance with a manifest spherical power correction requirement experienced by a subject of the corneal laser ablation.

2. The corneal laser ablation system of claim 1, wherein the corneal topography measuring instrument comprises a Placido ring imaging system.

3. The corneal laser ablation system of claim 1, wherein the corneal topography measuring instrument comprises a Scheimpflug imaging system.

4. The corneal laser ablation system of claim 1, wherein the corneal astigmatism derived at least in part from the topographical measurements made of the anterior corneal surface with the corneal topography measuring instrument comprises a cylinder power correction and an axis.

5. The corneal laser ablation system of claim 1, additionally comprising an axial eye length measuring instrument.

6. The corneal laser ablation system of claim 5, wherein the axial eye length measuring instrument comprises a laser interferometer.

7. The corneal laser ablation system of claim 1, wherein the measured corneal astigmatism derived at least in part from the topographical measurements is different in one or more of power and axis from a manifest astigmatism correction requirement experienced by a subject of the corneal laser ablation.

8. A corneal laser ablation system comprising:
a corneal topography measuring instrument;
a laser system configured to emit pulsed laser light at one or more wavelengths and configured to control the parameters of laser emission such that the laser output is suitable for controlled ablation of an anterior corneal surface;
wherein the laser system is configured to control the laser output to ablate at least some high order aberrations from the anterior corneal surface in accordance with topographical measurements of the anterior corneal surface made with the corneal topography measuring instrument;
wherein the laser system is configured to control the laser output to ablate the anterior corneal surface in a manner that reduces astigmatism of the anterior corneal surface in accordance with a corneal astigmatism derived at least in part from the topographical measurements of the anterior corneal surface made with the corneal topography measuring instrument; and
wherein the measured corneal astigmatism derived at least in part from the topographical measurements is different in one or more of power and axis from a manifest astigmatism correction requirement experienced by a subject of the corneal laser ablation.

9. The corneal laser ablation system of claim 8, wherein the topographically derived corneal astigmatism axis is at least 5 degrees different from the manifest astigmatism axis.

10. The corneal laser ablation system of claim 8, wherein the topographically derived corneal astigmatism power is at least 0.25 diopters different from the manifest astigmatism power.

11. The corneal laser ablation system of claim 8, wherein the corneal topography measuring instrument comprises a Placido ring imaging system.

12. The corneal laser ablation system of claim 8, wherein the corneal topography measuring instrument comprises a Scheimpflug imaging system.

13. The corneal laser ablation system of claim 8, wherein the corneal astigmatism derived at least in part from the topographical measurements made of the anterior corneal surface with the corneal topography measuring instrument comprises a cylinder power correction and an axis.

14. The corneal laser ablation system of claim 8, additionally comprising an axial eye length measuring instrument.

15. The corneal laser ablation system of claim 14, wherein the axial eye length measuring instrument comprises a laser interferometer.

16. A method of correcting corneal aberrations in an eye of a subject, the method comprising:
measuring a topography of a corneal surface of the subject;
obtaining a measurement of corneal astigmatism that is derived at least in part from the measured topography of the corneal surface;
planning a corneal laser ablation procedure based at least in part on the measurement of corneal astigmatism that is derived at least in part from the measured topography of the corneal surface;
performing corneal laser ablation on the corneal surface of the subject in accordance with the planning; and
determining a manifest astigmatism experienced by the subject and comparing the manifest astigmatism with the measured corneal astigmatism during the planning.

17. The method of claim 16, wherein the measuring is performed with a Placido ring imaging system.

18. The method of claim 16, wherein the measuring is performed with a Scheimpflug imaging system.

19. The method of claim 16, wherein the topographic measurement derived astigmatism is different in one or more of power and axis from the manifest astigmatism.

20. The method of claim 19, wherein the topographically derived astigmatism axis is at least 5 degrees different from the manifest astigmatism axis.

21. The method of claim 19, wherein the topographically derived astigmatism power is at least 0.25 diopters different from the manifest astigmatism power.

22. The method of claim 16, additionally comprising measuring the axial eye length of the eye of the subject.

23. The method of claim 22, comprising planning the corneal laser ablation procedure based at least in part on the measured axial eye length.

* * * * *